United States Patent [19]

Zuccarello et al.

[11] Patent Number: 5,445,805
[45] Date of Patent: Aug. 29, 1995

[54] LARGE POTASSIUM BICARBONATE CRYSTALS AND PROCESS FOR THE PREPARATION THEREOF

[75] Inventors: William Zuccarello, Allentown; Andrew D. Kurtz, Belle Mead; Lawrence Kirschner, Flanders; Herman Marder, Princeton, all of N.J.

[73] Assignee: Church & Dwight Co., Inc., Princeton, N.J.

[21] Appl. No.: 58,579

[22] Filed: May 6, 1993

[51] Int. Cl.$^6$ .................. C01D 7/40; A61K 33/00
[52] U.S. Cl. .................. 423/422; 23/302 R; 23/301; 424/715
[58] Field of Search .............. 23/302 R, 295 R, 301; 423/422; 424/715

[56] References Cited

U.S. PATENT DOCUMENTS

| | | | |
|---|---|---|---|
| 1,477,086 | 12/1923 | Suchy | 423/422 |
| 2,013,977 | 2/1932 | Weiss | 423/422 |
| 2,543,658 | 2/1951 | Durant et al. | 423/421 |
| 2,567,968 | 9/1951 | Saeman | 23/302 R |
| 2,721,209 | 10/1955 | Dauncey et al. | |
| 2,737,451 | 3/1956 | Saeman | 23/302 R |
| 2,768,060 | 10/1956 | Follows | 423/422 |
| 2,773,739 | 12/1956 | Burkholder | 423/422 |
| 2,792,283 | 5/1957 | Hill | 423/422 |
| 2,827,366 | 3/1958 | Saeman | 23/302 R |
| 2,926,995 | 3/1960 | Mod et al. | 423/422 |
| 3,141,730 | 7/1964 | LeBaron | 423/422 |
| 3,347,623 | 10/1967 | Schmid | 423/422 |
| 3,383,180 | 5/1968 | Kralik et al. | 23/302 R |
| 3,419,899 | 12/1968 | Tufts et al. | 23/302 R |
| 3,560,168 | 2/1971 | Stanton et al. | 23/302 |
| 3,630,692 | 12/1971 | Green et al. | 23/302 |
| 3,647,365 | 3/1972 | Saeman | 423/422 |
| 3,855,397 | 12/1974 | Hoffman et al. | 423/424 |
| 3,870,784 | 3/1975 | Saeman | 423/422 |
| 4,919,910 | 4/1990 | Kurtz et al. | 423/422 |
| 5,085,670 | 1/1992 | Quencer | 260/501 |
| 5,171,583 | 12/1992 | Morris, Jr. et al. | 424/717 |

FOREIGN PATENT DOCUMENTS 395134 10/1990 European Pat. Off. .

OTHER PUBLICATIONS

Perry, John H., Editor, Chemical Engineers Handbook McGraw-Hill Book Co, New York, N.Y. 1950 pp. 1050–1071.

Kirt Othmer Encyclopedia of Chemical Technology Third Edition, 1982, no month available, vol. 7, pp. 243–279 and vol. 18, pp. 922–923 and 936–937.

Gmelin Handbuch (1938), vol. 22, pp. 857–865.

Primary Examiner—Gary P. Straub
Attorney, Agent, or Firm—Bryan Cave

[57] ABSTRACT

A large size, small surface area, granular crystalline potassium bicarbonate product suitable for application as an active ingredient in pharmaceutical oral unit dosage forms useful for the treatment of various degenerative bone and cardiovascular diseases, particularly osteoporosis or hypertension, comprising potassium bicarbonate crystals having a mean particle size of at least 350 microns and a specific B.E.T. surface area less than 0.02 m$^2$/gram. A process for preparing such product is further provided, in which a solution of potassium bicarbonate is fed to a slurry of potassium bicarbonate crystals in a crystallizer and the temperatures and concentrations of the potassium bicarbonate in the feed solution and the crystallizer slurry are so regulated, and the residence time and degree of agitation in the crystallizer are so controlled, that the desired large size, small surface area potassium bicarbonate crystals are produced.

3 Claims, 4 Drawing Sheets

LARGE POTASSIUM BICARBONATE CRYSTALS AND PROCESS FOR THE PREPARATION THEREOF

BACKGROUND OF THE INVENTION

1. Field of the Invention

This invention relates to large size, small surface area granular crystals of potassium bicarbonate particularly useful as active ingredients of pharmaceutical oral dosage forms for potassium supplementation and for the treatment of degenerative bone or cardiovascular diseases, e.g., osteoporosis and hypertension, and to a process for the preparation of such crystals.

Potassium bicarbonate is a well-known commodity of commerce having various uses, e.g., in baking powders, as an effervescent salt in soft drinks, as a fire-extinguishing agent, and in various pharmaceutical applications, for example, in the treatment of excess acidity. Presently, potassium bicarbonate is available in commercial quantities in the form of very fine crystals or agglomerates, which are irregularly shaped, have rough surfaces, exhibit poor packing and flow characteristics and may be subject to dusting or caking problems.

One current commercially available potassium bicarbonate product, marketed as "Coarse Granular Potassium Bicarbonate" by Armand Products Co., Princeton, N.J., U.S.A., comprises irregularly shaped, rough-surfaced crystals with few agglomerates, which has a mean particle size of about 180 microns, essentially no individual crystals larger than 300 microns and a B.E.T. specific surface area of 0.06 $m^2$/gram. A second commercial product, available from Mallinckrodt Specialty Chemicals Co., St. Louis, Mo., U.S.A., as "Potassium Bicarbonate USP Granular TAC", comprises similar irregularly shaped, rough-surfaced and non-agglomerated crystals and has a mean particle size of about 180 microns with essentially no individual crystals larger than 420 microns and a B.E.T. surface area of 0.02 $m^2$/gram. A third currently available product, "Alphapur Granular Potassium Bicarbonate" produced by SCPA of Paris, France, is a rough-surfaced, largely agglomerated product having a mean particle size of about 300 microns and a B.E.T. surface area of 0.02 $m^2$/gram. If separated by screening into varying size fractions, about 10% of this product comprises agglomerates having sizes within the range of 600 to 850 microns with a B.E.T. surface area of 0.018 $m^2$/gram.

It has recently been proposed to use potassium bicarbonate as an active ingredient for the treatment of osteoporosis or hypertension. See Morris et al U.S. Pat. No. 5,171,583 granted Dec. 15, 1992, and PCT Published Application No. PCT/US89/04771. The potassium bicarbonate crystals of the present invention are particularly suitable for oral dosage forms useful in this last mentioned application. They are also useful in other applications, e.g., for agricultural uses, or where it is important to avoid dust formation or caking.

The effective oral dosage of potassium bicarbonate in the treatment of osteoporosis or hypertension is about 40–400 mmoles, preferably about 40–250 mmoles, per 70 kg patient weight per day. In a particularly preferred embodiment, the potassium bicarbonate is administered at a dose of 60 mmoles (6 grams) per day. When, for example, the potassium bicarbonate is administered in the form of four tablets daily, each such preferred oral dosage form should incorporate 1.5 grams of the potassium bicarbonate. Since potassium bicarbonate has a bitter taste and is irritating to the gastrointestinal mucosa, the potassium bicarbonate must be coated with a controlled release coating masking its taste and facilitating controlled release in the G.I. tract over an extended time period.

For ease of swallowing, solid dosages of drugs intended for chronic administration to humans should not possess total volumes of more than about one milliliter. When 1.5 grams of current commercially available, small particle size granular (unagglomerated) potassium bicarbonate particles are tabletted, with a release coating having a density of about 1/gram/ml., the resulting dosage form has a significantly greater volume. Clearly, such a tablet would be hard to swallow and would not meet with good patient acceptance, particularly in any product used in the treatment of a chronic disease. It has thus been found critical, in accordance with the present invention, to provide potassium bicarbonate crystals having markedly greater particle sizes and markedly decreased specific surface areas as compared with currently available potassium bicarbonate crystalline products.

Various processes have been described in the patent literature for preparing potassium bicarbonate. None of the references which have been noted make any specific mention of the formation of large particle size, small surface area potassium bicarbonate crystals. See, for example, U.S. Pat. Nos. 1,477,086; 2,013,977; 2,543,658; 2,768,060; 3,141,730; 3,347,623; and 4,919,910. On the other hand, a number of procedures have been specifically described in the patent literature for producing coarse crystals of sodium bicarbonate or other salts. See, for example, U.S. Pat. Nos. 2,773,739; 2,792,283; 2,926,995; 3,647,365; 3,855,397; 3,870,784; EP Published Application No. 395,134 [sodium bicarbonate]; U.S. Pat. No. 2,721,209 [ethylene diamine tartrate]; and U.S. Pat. No. 5,085,670 [potassium chloride]. Crystallization is, however, an empirical art and procedures utilized for growing crystals of one substance often do not work for another.

Thus, procedures described in the literature for producing coarse sodium bicarbonate crystals have not been found useful for forming large, pure potassium bicarbonate crystals. Conversely, the procedures described below for the formation of large, low surface area potassium bicarbonate crystals have not been as successful in forming large sodium bicarbonate crystals since the latter material tends to nucleate during crystallization with the formation of crystals having minute particle sizes. In addition, crystal growth modifiers (which may be employed in conventional commercial manufacturing operations) may not be suitable in the production of potassium bicarbonate utilized in pharmaceutical products due to the stringent purity requirements for such products.

It is, accordingly, among the objects of the present invention to provide large size, small surface area potassium bicarbonate crystals which may be efficiently produced in commercial quantities and which may be formulated in orally administrable dosage forms useful for pharmaceutical applications and, in particular, in dosage forms suitable in the treatment of osteoporosis or hypertension. A further object of the invention is the provision of a process for the preparation of such large potassium bicarbonate crystals which may be efficiently utilized in the commercial production of such dosage forms. Other objects and advantages of the invention will be apparent from the following description.

SUMMARY OF THE INVENTION

It has been found possible, in accordance with the present invention, to provide large size, small surface area granular (i.e., unagglomerated) potassium bicarbonate crystalline products having mean particle sizes (average particle sizes, by weight) of at least about 350 microns and up to as large as about 3000 microns, preferably within the range of about 500–1200 microns; and small specific surface areas, i.e., B.E.T. surface areas less than about 0.02 m$^2$/gram, preferably less than about 0.015 m$^2$/gram.

Most desirably, the potassium bicarbonate crystals of the invention which are useful as active ingredients of pharmaceutical oral dosage forms for potassium supplementation and for the treatment of degenerative bone and cardiovascular diseases such as osteoporosis and hypertension, have a mean particle size within the range of about 800–900 microns, a specific B.E.T. surface area of about 0.004–0.01 m$^2$/gram and a particle size distribution such that over 90 wt. % of the crystals have particle sizes within the range of about 700–1000 microns.

The crystals of the invention may be used to provide multiple-particle oral dosage forms containing 15 mmoles (1.5 grams) of the potassium bicarbonate active ingredient, with total volumes of about 1 ml. The use of such oral dosage forms assures patient compliance in the high dosage potassium bicarbonate regimens requisite in the treatment of osteoporosis or hypertension. Moreover, the large size, granular crystals are particularly useful in the subsequent processing required for the preparation of pharmaceutical dosage forms. Hence, as distinguished from currently available agglomerated materials (which crumble upon compression), they may be subjected to the strong compressive forces utilized in tabletting operations without appreciable change in particle size or surface area. In addition, the larger inertial forces required to impel the large crystals (as compared with smaller potassium bicarbonate crystals) simplifies processing thereof, e.g., by easing control of fluidized bed drying operations, minimizing dusting problems, etc.

Preferably, the potassium bicarbonate crystals of the invention possess unagglomerated, "blocky" shapes, i.e., they are shaped like regular solids having substantial sizes in all three dimensions, as distinguished from distinctly needle-, fiber- or platelet-like shapes, and have relatively smooth surfaces. When coated with a controlled release coating, formulated with the usual excipients and compressed into a tablet, such crystals pack well and leave relatively minute interstitial voids therebetween.

The large size, small surface area, granular, potassium bicarbonate crystals hereof are produced, in accordance with a further feature of the invention, by a novel process designed both to maximize the particle size and minimize the specific surface area of the crystals, and, preferably, to produce the crystals in the foregoing unagglomerated (granular), blocky, smooth-surfaced shapes. In accordance with this process the large crystals of the invention are obtained by (a) feeding an aqueous solution of potassium bicarbonate at an elevated temperature $T_1$ and a concentration below the saturation point at $T_1$, to a slurry of potassium bicarbonate crystals in a crystallizer, the temperature $T_2$ of the slurry being below the saturation temperature of the feed solution, and the concentration of the feed solution and the temperatures $T_1$ and $T_2$ being such that the degree of supersaturation in the liquid phase of the slurry is kept relatively low causing the size of the crystals in the slurry to grow without a high degree of nucleation;

(b) feeding the potassium bicarbonate solution to the slurry at a rate such that the residence time in the crystallizer is sufficient for the potassium bicarbonate crystals to grow into the large crystals;

(c) maintaining the potassium bicarbonate slurry in the crystallizer under mild agitation sufficient to suspend the potassium bicarbonate solids without foaming the slurry or degrading the crystals; and (d) separating and recovering the large crystals from the slurry.

By carrying out the crystallization in this manner, both primary nucleation and secondary nucleation of the potassium bicarbonate slurry are minimized, and the potassium bicarbonate crystals initially present in the slurry are permitted to grow into the desired large crystals having substantially uniform particle size distributions. Primary nucleation, i.e., the normal precipitation of the potassium bicarbonate by reason of the temperature and concentration fluxes in the crystallizer slurry, is minimized by maintaining the potassium bicarbonate feed solution at less than saturation concentrations and providing a long residence time in the crystallizer. In this manner, the feed stream does not nucleate when it is introduced into the crystallizer slurry and, because of the substantial dilution effect upon introduction into the crystallizer, the dissolved potassium bicarbonate in the feed does not precipitate and form independent nuclei. At the same time, secondary nucleation, i.e., rapid separation and mechanical breakage of the crystals in the slurry, does not occur, the degree of agitation in the crystallizer slurry being carefully controlled to avoid the formation of secondary crystal nuclei. In this manner, crystal growth in the slurry takes place primarily, if not exclusively, on the potassium bicarbonate crystals initially present in the slurry, thus permitting precise control of both the size and particle size distribution of the product crystals.

Preferably, in order to assure preparation of the crystalline product of the present invention, the potassium bicarbonate crystals in the initial slurry in the crystallizer are obtained by seeding. The seed crystals may be of any type, e.g., conventional commercial potassium bicarbonate particles having a particle size range of about 50–300 microns ($-50/+270$ mesh), and a substantially uniform particle size distribution such that at least 80 wt. % of the crystals have a particle size range of about 100–200 microns ($-70/+140$ mesh). It will be appreciated that the slurry may be seeded with potassium bicarbonate crystals having other particle sizes and size distributions, in which case the amount of seed introduced will be modified in order to produce the requisite large and substantially uniform particle size potassium bicarbonate crystals of the invention.

Potassium bicarbonate is in equilibrium with potassium carbonate, water and carbon dioxide, in accordance with the following equation:

In order to maximize the concentration of potassium bicarbonate present and prevent the formation of potassium carbonate, it is preferred to add carbon dioxide to the feed tank or the crystallizer. The $CO_2$ may either be bubbled into the potassium bicarbonate feed or slurry, both to maintain the desired equilibrium and as a processing aid; or it may be introduced in the form of a blanket over the slurry.

In accordance with another feature of the invention, the water-wet potassium bicarbonate crystals recovered from the crystallizer slurry may be washed, prior to drying, with methanol. The methanol removes any liquor clinging to the crystals and leaves smooth, impurity-free surfaces thereon. The methanol may then be removed by conventional drying techniques.

Employing the foregoing process, the particularly desirable large size, small surface area granular potassium bicarbonate crystals of the invention are formed in a single pass, in yields of about 5% or more. Utilizing a closed loop operation with continuous recycle, substantially complete conversion to the desired product is achieved. Further, the potassium bicarbonate crystals are prepared in high purity, readily satisfying USP requirements for pharmaceutical products. They possess higher purities than the commercially available potassium bicarbonate starting materials, since they are prepared by recrystallization thereof (and without the necessity for the addition of any crystal growth modifiers). Moreover, the relatively small surface area of the crystalline products of the invention minimizes the presence of surface-adsorbed impurities, e.g., potassium carbonate. Thus, the crystals are substantially free of any potassium carbonate impurity, i.e., they contain less than about 1.0 wt. % and, preferably, less than about 0.5 wt. %, potassium carbonate.

Other features of the present invention will be apparent from the following description of preferred embodiments of the large potassium bicarbonate crystals and crystal-forming process hereof, taken in connection with the accompanying drawing in which:

DETAILED DESCRIPTION OF THE INVENTION

As indicated hereinabove, the particularly desirable potassium bicarbonate crystal products of the invention which are useful in pharmaceutical oral dosage forms, have mean particle sizes within the range of about 800–900 microns, specific B.E.T. surface areas of about 0.004–0.01 $m^2$/gram and particle size distributions such that over 90 wt. % of the crystals have particle sizes within the range of about 700–1000 microns. These particularly preferred crystals are desirably in unagglomerated, blocky forms, the particular shapes of which may vary depending upon the individual crystal sizes and the degree of agitation utilized in the crystallizer. The crystal shapes thus vary from forms having relatively sharp corners approximating the ideal shape of a parallelepiped or cube, to forms having moderately rounded corners (due to attrition caused by friction of the crystals against the surfaces of the crystallizer or one another), to ellipsoidal shapes, spherical shapes or even columnar shapes having rounded ends (in the case of the largest crystals and/or crystals formed with the highest degrees of agitation).

When prepared in accordance with the present process involving the use of long residence times and low degrees of agitation in the potassium bicarbonate crystallizer, the blocky crystals possess particularly smooth surfaces which are of importance for various applications. Such particles have minimum specific surface areas. Alternatively, the crystallization parameters may be varied, e.g., by increasing the degree of agitation of the potassium bicarbonate slurry in the crystallizer, to roughen the crystal surfaces somewhat. Accordingly, it will be understood that the degree of smoothness of the potassium bicarbonate crystals of the invention may be varied as desired.

The process features of the invention may be considered in the context of the four successive steps of (a) feeding a potassium bicarbonate solution into a potassium bicarbonate slurry under specific temperature and concentration conditions; (b) feeding the solution to the slurry at a rate sufficient to establish particular residence times in the crystallizer; (c) maintaining mild conditions of agitation in the crystallizer; and (d) separating and removing the resulting desired potassium bicarbonate crystal product:

(a) Feeding the Potassium Bicarbonate Solution Into the Slurry Under Particular Temperature and Concentration Conditions As indicated above, the process hereof is initiated by feeding an aqueous solution of potassium bicarbonate at an elevated temperature $T_1$ and a concentration below the saturation point of $T_1$, to a slurry of potassium bicarbonate crystals in a crystallizer, the temperature $T_2$ of the slurry being below the saturation temperature of the feed solution, and the concentration of the feed solution and the temperatures $T_1$ and $T_2$ being such that the degree of supersaturation in the liquid phase of the slurry is kept relatively low, causing the size of the crystals in the slurry to grow without a high level of primary nucleation.

The aqueous potassium bicarbonate solution to be fed to the crystallizer (the "feed liquor") is controlled at a temperature $T_1$ of, for example, about 40° to 90° C. or up to 200° C. at superatmospheric pressure, preferably about 50° C. to 70° C. at atmospheric pressure. The feed solution has a potassium bicarbonate concentration of, e.g., at least about 0.5 wt. % below, preferably from about 1 to 5 wt. % below, the saturation concentration of the solution at $T_1$. In absolute terms, the potassium bicarbonate concentration of the feed liquor may be, e.g., about 20 to 50 wt. %, preferably about 35 to 50 wt. % of potassium bicarbonate at atmospheric pressure.

The slurry in the crystallizer to which the feed liquor is fed, is at a temperature $T_2$ which is about 10° to 70° C. below, preferably about 30° to 50° C. below, the temperature $T_1$ of the potassium bicarbonate feed liquor fed to the crystallizer. In absolute terms, $T_2$ may be, e.g., about 0° to 50° C., preferably about 15° to 35° C. The slurry density of the slurry in the crystallizer, i.e., the weight percent of the solid crystals in the slurry, will depend on the values of the potassium bicarbonate concentration of the feed liquor, and temperatures $T_1$ and $T_2$. Typically, the slurry density will be in the range of about 10 to 30 wt. %. The composition of the slurry should be maintained so that potassium bicarbonate is at all times the stable solid phase.

Figure 1:
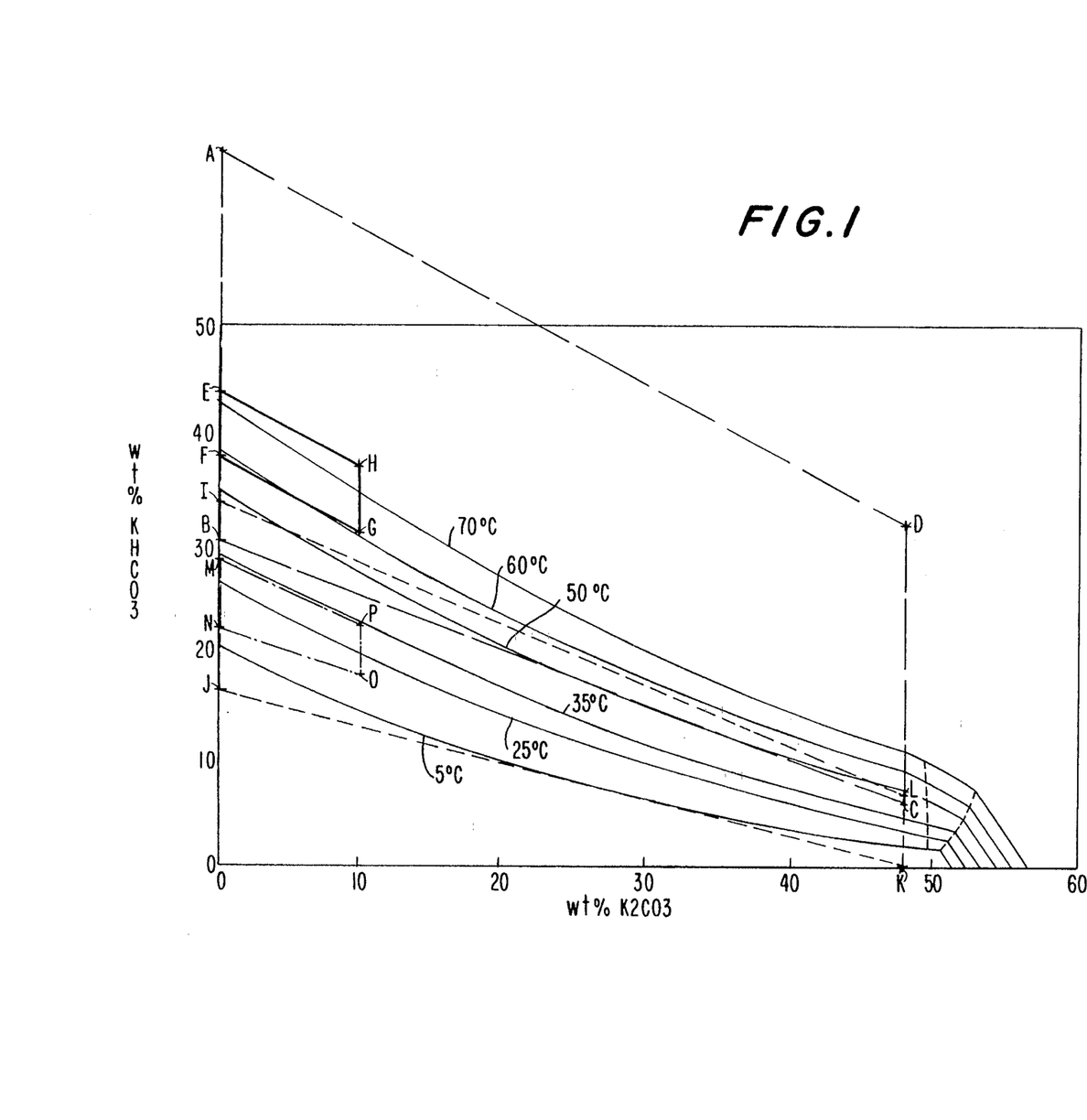
FIG. 1 is a phase diagram of the potassium bicarbonate/potassium carbonate system, indicating the broad and preferred ranges of compositions of the potassium bicarbonate feed solution and the initial crystal slurry which may be utilized for preparing the large, substantially uniform particle size potassium bicarbonate crystals in accordance with this invention.

The ranges of potassium bicarbonate concentrations in the feed liquor and the crystallizer slurry which may be utilized in the process of the invention are shown in FIG. 1, a potassium bicarbonate/potassium carbonate phase diagram. As illustrated, the potassium bicarbonate concentrations in the feed liquor are within region A,B,C,D of the phase diagram (indicated by dotted lines), preferably within region E,F,G,H (indicated by solid lines). The potassium bicarbonate concentrations in the crystallizer are within region I,J,K,L of the diagram (indicated by dotted lines), preferably within region M,N,O,P thereof (indicated by solid lines).

The initial feed liquor is preferably prepared by dissolving in water conventional potassium bicarbonate crystals having a size and/or shape different from that of the desired crystals to be produced, to obtain the desired concentration, and bringing the solution to the desired temperature. Alternatively, the feed solution may be obtained as an intermediate stream in the commercial production of potassium bicarbonate altered, if necessary, by the addition of potassium bicarbonate or water to the solution, and heating or cooling the solution so as to obtain a feed liquor at the desired temperature and concentration.

The initial slurry in the crystallizer may be prepared by dissolving commercial potassium bicarbonate in water to obtain a potassium bicarbonate concentration which is saturated at $T_2$, cooling the solution to $T_2$, and dispersing additional seed crystals of potassium bicarbonate to obtain a suitable slurry. Alternatively, the initial slurry may be obtained by adding feed liquor to a saturated solution in the crystallizer at $T_2$ to precipitate potassium bicarbonate and form the slurry, removing slurry from the crystallizer, separating crystals from the slurry, recycling the crystals to the crystallizer, and recycling the excess liquor to the feed tank. This procedure is continued until the slurry in the crystallizer contains crystals having the desired particle size distribution, after which the crystallization is initiated.

When the feed liquor is added to the crystallizer slurry, it is rapidly mixed with the liquid phase of the slurry which is supersaturated. The feed liquor contains a substantially higher potassium bicarbonate concentration than the supersaturated liquor phase of the crystallizer slurry. However, since the feed liquor is somewhat unsaturated at its temperature $T_1$, the addition of the feed liquor to the slurry does not produce so large an increase in the localized level of supersaturation of the slurry liquid phase as might cause an undesirably large amount of nucleation. Thus, the relatively modest rise in the overall level of supersaturation of the liquid phase of the slurry contributes primarily to the growth of existing crystals rather than to the formation of new crystals by primary nucleation.

The process is preferably carried out continuously, during which most of the water and some of the makeup potassium bicarbonate in the feed liquor is obtained by recycling to the feed tank the mother liquor remaining after the desired large potassium bicarbonate crystals have been separated from the slurry withdrawn from the crystallizer. Another recycle stream may be heated to dissolve any small crystals withdrawn from the crystallizer prior to recirculation, the recycle thus serving as a fines destruction loop.

As indicated above, carbon dioxide may also be sparged into or utilized to blanket the solution in the feed tank and/or the slurry in the crystallizer, in order to regulate the potassium bicarbonate/potassium carbonate equilibrium and thus minimize the formation of the latter and maintain the high purity of the final potassium bicarbonate crystal product.

(b) Establishing the Residence Time in the Crystallizer

As further noted above, the potassium bicarbonate solution is fed into the slurry in the crystallizer at a rate such that the residence time in the crystallizer is sufficient for the potassium bicarbonate particles to grow into the desired large crystals, e.g., to crystals having particle sizes of from about 600-1200 microns which pass through a No. 16 U.S. Mesh screen and are retained on a No. 30 screen). The rates of feed liquor fed to the crystallizer and slurry withdrawn from the crystallizer are such that the "turnover" (T.O.) or residence time, i.e., the period of time to feed a volume equal to the volume of slurry present in the crystallizer in continuous operation, is, e.g., about 0.5 to 10 hours, preferably about 3 to 6 hours.

Large turnover or residence times are obtained by limiting the rate of introduction of the feed liquor to a small fraction of the volume of the slurry in the crystallizer, e.g., to from 1/30 to 1/600 the volume of the slurry per minute. In this manner, the slurry is maintained in the crystallizer for a relatively long time, facilitating the desired growth of the initial potassium bicarbonate crystals and ensuring sufficient dilution of the feed stream as to minimize primary nucleation thereby.

(c) Maintaining Mild Agitation Conditions in the Crystallizer

As indicated, the potassium bicarbonate slurry in the crystallizer is maintained under mild agitation conditions such that secondary nucleation and significant crystal breakage are avoided. The agitation should be sufficient to suspend the potassium bicarbonate solids without beating the slurry into a foam or froth. The appropriate degree of agitation may be empirically determined by withdrawing samples from the crystallizer under different degrees of agitation and examining the crystals microscopically for evidence of breakage.

(d) Separating and Removing the Potassium Bicarbonate Crystal Product

The slurry withdrawn from the crystallizer is subjected to a separation treatment, e.g., centrifugation, and the separated crystals are dried and classified by mesh size. Crystals which are larger or smaller than desired may be destroyed (dissolved) and recycled along with the mother liquor from the separation treatment to feed liquor preparation.

It will be understood that the process of the present invention may be utilized to produce other large potassium bicarbonate crystals having sizes in the 350–1700 micron range and in varying forms, e.g., in fiber-, needle- or platelet-like shapes. Such products may be produced by varying the process parameters, e.g., the residence time and degree of agitation of the slurry in the crystallizer.

Figure 2:
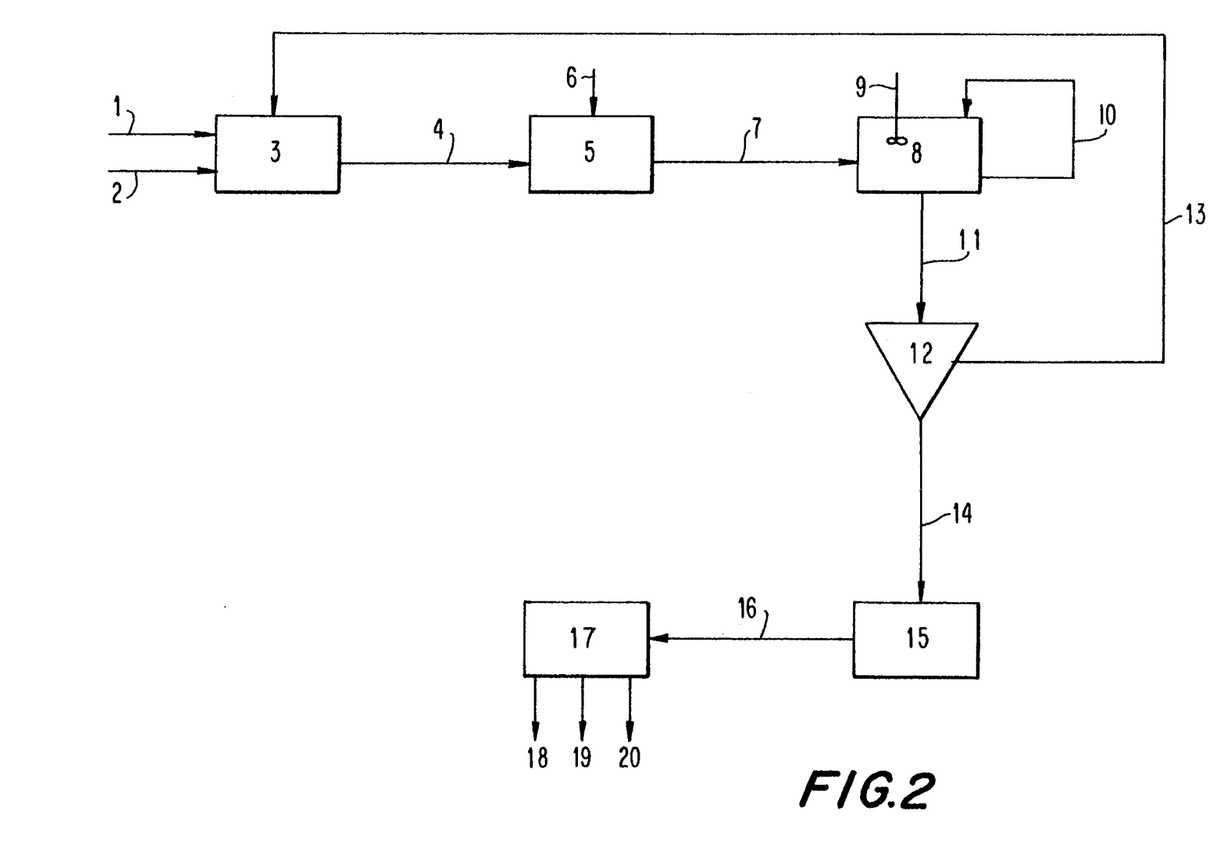
FIG. 2 is a schematic diagram of a flow sheet of a continuous process for preparing the potassium bicarbonate crystals in accordance with the process features of the invention.
Figure 3:
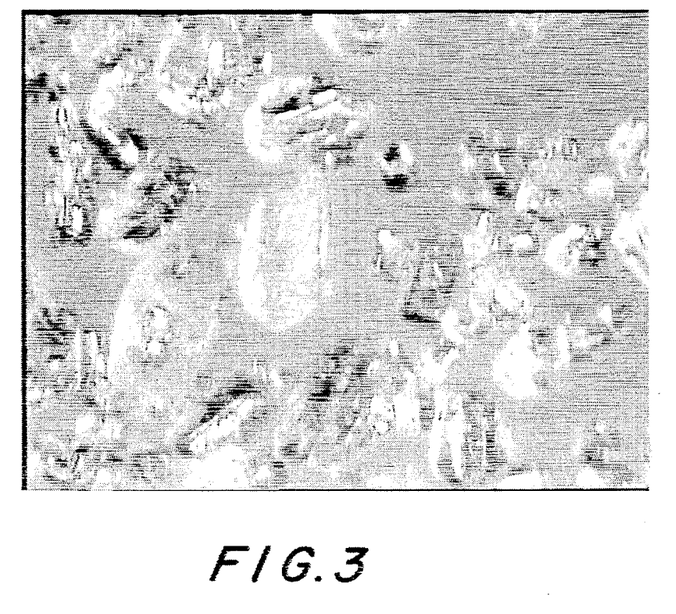
FIG. 3 is a photomicrograph (at about 25X magnification) of a current commercial potassium bicarbonate product, viz., "Coarse Granular Potassium Bicarbonate" available from Armand Products Co., a joint venture of the assignee of the present invention.
Figure 4:
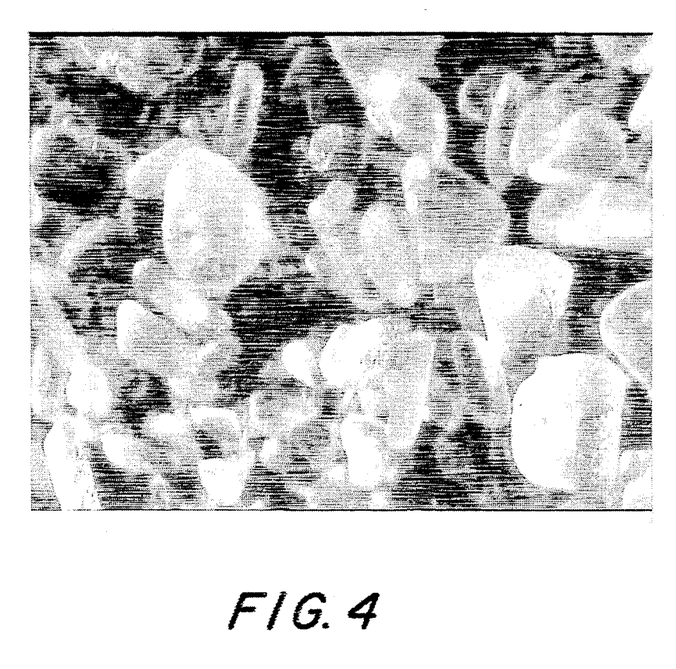
FIG. 4 is a similar photomicrograph (also at 25X magnification) of a further current commercial potassium bicarbonate product, viz., "Potassium Bicarbonate USP Granular TAC" distributed by Mallinckrodt Specialty Chemicals Co.

The process hereof is preferably carried out continuously, with continuous introduction of the feed liquor into the crystallizer, withdrawal of the slurry from the crystallizer for separation of the potassium bicarbonate product crystals and recycle of a portion of the mother liquor from the crystallizer. A preferred system for carrying out the process in such a manner is illustrated in FIG. 2. Referring to that figure, makeup commercial potassium bicarbonate is fed through line 1, makeup water is fed through line 2, and recycled mother liquor is fed through line 13 to dissolver 3 where an initial feed composition is prepared containing potassium bicarbonate and water. The initial composition is fed through line 4 to feed tank 5 where it is maintained at a predetermined temperature, $T_1$, and a potassium bicarbonate concentration which is somewhat lower than the saturation concentration at that temperature, suitable for feeding to the crystallizer. A carbon dioxide stream 6 may also be introduced into the feed tank, either as a processing aid or to provide a $CO_2$ blanket over the feed solution.

The resulting feed liquor is fed through line 7 to crystallizer 8 containing a slurry of crystals mildly agitated by mixer 9 and maintained at a temperature $T_2$ substantially lower than that of the feed liquor. Although the feed liquor is somewhat unsaturated, its concentration is substantially higher than that of the liquid phase of the slurry in the crystallizer resulting in an incremental increase in the supersaturation of the slurry and growth of the slurry crystals with a minimum of nucleation due to the unsaturation of the feed liquor. A fines destruction loop 10 is provided in which the fines-containing mother liquor may be separated from the slurry, reheated to dissolve the fines and recirculated to crystallizer 8.

Slurry containing crystals having the desired particle size distribution is continuously or periodically withdrawn from crystallizer 8, and fed through line 11 to centrifuge 12 where wet crystals are separated from mother liquor which is recycled to dissolver 3 through line 13. An alcohol, e.g., methanol, may be used to wash the crystals.

The wet crystals are transferred by conveyance 14 to dryer 15, where they are dried, and the dry crystals are transferred by conveyance 16 to classifier 17, where they are separated into different mesh sizes, e.g., three sized fractions as indicated in the drawing, which are withdrawn by conveyances 18, 19 and 20.

Although the preferred form of the process of this invention is continuous as illustrated in FIG. 2, it may also be advantageous under certain circumstances to practice the process batchwise. Thus, the feed liquor may be fed to the crystallizer slurry in the absence of any continuous or periodic partial withdrawal of the slurry from the system for separation and recovery of crystals, and the slurry can then be cooled until the particle sizes and size distribution of the slurry crystals reaches the desired point. The entire batch of slurry may then be withdrawn from the crystallizer and treated to separate and recover the crystals as described. Such a batch operation may be carried out with or without external circulation of the crystal slurry for fines destruction.

The following example further illustrates the invention. As used in the example and elsewhere in this specification, mean particle sizes are determined by weight of the respective crystal products, and specific surface areas are determined by the B.E.T. method.

EXAMPLE

A mother liquor was prepared by charging 3500 pounds of commercially available potassium bicarbonate to 1330 gallons of deionized water, heating the feed composition to a temperature of 45° C. within dissolver 3 until fully dissolved, and transferring the composition through an inline filter to the crystallizer 8. This mother liquor was then cooled to between 15° and 21° C. at which point it was seeded with 25 pounds of commercially available potassium bicarbonate.

A feed liquor was prepared by charging 3165 pounds of potassium bicarbonate to 646 gallons of deionized water in the dissolver, heating the mixture to a temperature of 69°–70° C. and maintaining it at that temperature to keep all of the potassium bicarbonate in solution. At these temperatures, the feed liquor maintains a slight degree of unsaturation, which is necessary to minimize nucleation in the crystallizer.

Feed liquor was then transferred through line 7 to the crystallizer at about 5 gallons per minute (GPM) through an inline filter with a 1 micron filter cartridge. This feed rate was achieved by regulating the feed solution through a rotameter and pump recycle line. A sample of the feed solution was analyzed every hour to monitor the carbonate and bicarbonate contents. When the results indicated higher than desirable levels of carbonate, carbon dioxide was slowly charged from cylinders into the pump recycle line.

The crystallizer 8 was a 2000 gallon glass-lined jacketed reactor with a single impeller agitator rotating at 80 revolutions per minute (RPM). The average working volume of the crystallizer was about 1650 gallons; therefore, the retention time was about 5½ hours.

Slurry from the crystallizer was centrifuged on a semi-continuous basis through a perforated basket type centrifuge 12 on a 75 minute cycle after beginning the transfer of the feed liquor through line 7. Approximately 300 gallons of centrifugate and 450 pounds of crystals were obtained in each cycle. The mother liquor was then recycled to the dissolver through line 13 where it was charged with potassium bicarbonate, heated to a temperature between 69° and 71° C. until fully dissolved, and then transferred to the feed tank 5.

Centrifuge wetcake can alternately be washed with methanol, in which the potassium bicarbonate is sparingly soluble, to aid the dewatering and drying processes. In the present example, 5 gallons of methanol were applied to about 450 pounds of wetcake, and the wash discharged to waste. Care was taken to avoid contamination of the mother liquor.

Crystals of potassium bicarbonate were unloaded from the centrifuge into lined 35 gallon fiber drums. After the centrifuge was emptied, it was rinsed with 30 gallons of deionized water which was thereafter discharged to waste. The crystals were charged batchwise to a dryer 15 and dried at 50° C. to 60° C. for a 4-hour period under vacuum with a nitrogen purge.

A typical crystal product recovered from the centrifuge incorporated the following crystal yields determined as weight fractions after screening. Dryer product yields were somewhat reduced due to attrition under non-optimal conditions:

| Particle Sizes (microns) | Yield (% by weight) |
|---|---|
| 900 ± 100 | 10% |
| 700 ± 100 | 30% |
| 800 ± 200 | 40% |
| 700 ± 200 | 50% |

Figure 5:
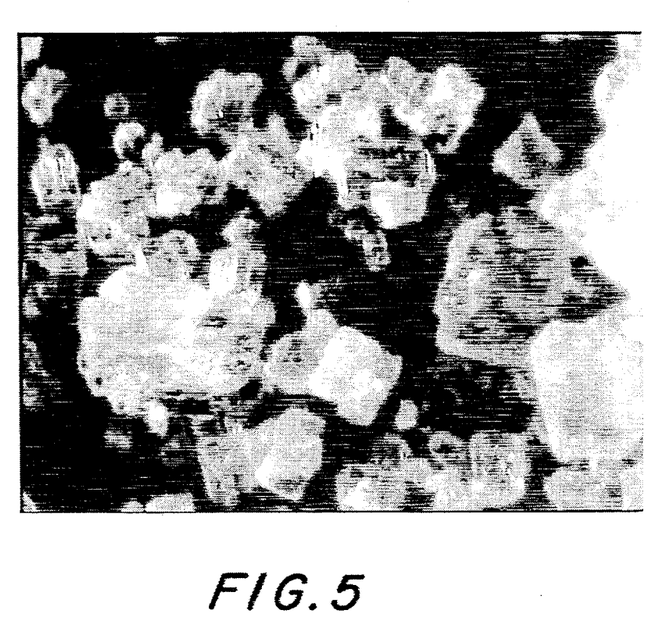
FIG. 5 is a photomicrograph (again, at 25X magnification) of a third currently available commercial potassium bicarbonate product, viz., "Alphapur Granular Potassium Bicarbonate" produced by SCPA.
Figure 6:
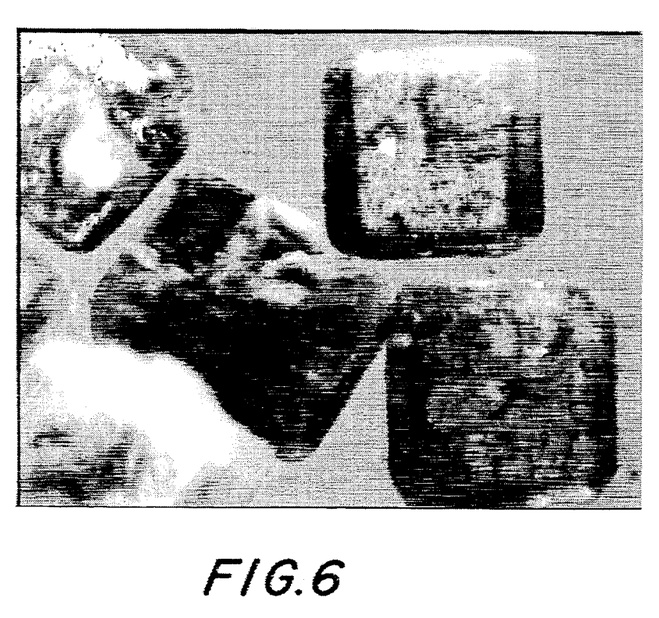
FIG. 6 is a photomicrograph (again, at 25X magnification) of blocky, generally cubic smooth-surfaced crystals of the present invention, which possess a large mean particle size (about 800 microns), minimal agglomeration and low specific B.E.T. surface area (about 0.005–0.006 $m^2$/gram).

The 800 micron fraction produced as described above comprises crystals similar to those illustrated in FIG. 5 above, viz., blocky, cubic, smooth-surfaced crystals possessing low specific B.E.T. surface areas and minimal agglomeration, and being particularly suitable for the preferred pharmaceutical application of the present invention.

Although the present invention has been described in detail by way of illustration and example for purposes of clarity and understanding, it will be understood that various changes and modifications may be carried out within the scope of the claims appended hereto.

We claim:

1. A crystalline potassium bicarbonate product suitable for application as an active ingredient in oral pharmaceutical dosage forms, comprising unagglomerated, blocky-shaped crystals having a weight mean particle size of at least 350 microns and a specific B.E.T. surface area less than 0.02 $m^2$/gram.

2. The crystalline potassium bicarbonate product of claim 1, having a weight mean particle size within the range of 500–1200 microns and a specific B.E.T. surface area less than 0.015 $m^2$/gram.

3. The crystalline potassium bicarbonate product of claim 1, having a weight mean particle size within the range of 800–900 microns, a specific B.E.T. surface area of 0.004–0.01 $m^2$/gram and a particle size distribution such that over 90 wt. % of the crystals have particle sizes within the range of 700–1000 microns.

* * * * *